(12) United States Patent
Harrison et al.

(10) Patent No.: US 9,456,921 B2
(45) Date of Patent: *Oct. 4, 2016

(54) CLEAR, WASHABLE LUBRICANT COMPOSITIONS AND METHODS OF MAKING SAME

(75) Inventors: James Jeffries Harrison, West Hills, CA (US); Guillermo Hernandez, Chatsworth, CA (US)

(73) Assignee: CHEMSIL SILICONES, INC., Chatsworth, CA (US)

( * ) Notice: Subject to any disclaimer, the term of this patent is extended or adjusted under 35 U.S.C. 154(b) by 251 days.

This patent is subject to a terminal disclaimer.

(21) Appl. No.: 13/482,811

(22) Filed: May 29, 2012

(65) Prior Publication Data
US 2012/0294820 A1 Nov. 22, 2012

Related U.S. Application Data (63) Continuation-in-part of application No. 12/586,198, filed on Sep. 18, 2009.

(60) Provisional application No. 61/113,623, filed on Nov. 12, 2008, provisional application No. 61/200,290, filed on Nov. 26, 2008.

(51) Int. Cl.
| | |
|---|---|
| *C10M 169/04* | (2006.01) |
| *C08G 63/00* | (2006.01) |
| *A61K 8/19* | (2006.01) |

(Continued)

(52) U.S. Cl.
CPC ............... *A61F 6/04* (2013.01); *A61K 8/345* (2013.01); *A61K 8/37* (2013.01); *A61K 8/4946* (2013.01); *A61K 8/8152* (2013.01); *A61K 8/8158* (2013.01); *A61K 8/891* (2013.01); *A61Q 9/02* (2013.01); *A61Q 19/00* (2013.01)

(58) Field of Classification Search
CPC .................. C10M 2229/04; C10M 2229/041; A61Q 9/02; A61K 9/0014
USPC .......................... 508/208, 494; 424/73, 78.02
See application file for complete search history.

(56) References Cited

U.S. PATENT DOCUMENTS

| 4,389,418 A | 6/1983 | Burton |
| 4,801,447 A | 1/1989 | Gum |

(Continued)

FOREIGN PATENT DOCUMENTS

| CN | 104825371 | 8/2015 |
| JP | 7267849 A | 10/1995 |
| JP | 10182432 A | 7/1998 |

OTHER PUBLICATIONS

Sun et al., "Refractive index matching and clear emulsion", J. Cosmet. Sci., 56, pp. 253-265, (Jul./Aug. 2005).

(Continued)

*Primary Examiner* — Vishal Vasisth
(74) *Attorney, Agent, or Firm* — Stout, Uxa & Buyan, LLP; Carlos A. Fisher (57) ABSTRACT

Bi- or multiphasic, clear or translucent silicone-containing lubricant compositions, and products including such compositions and methods of making such compositions and products are disclosed. The refractive index of each immiscible phase of the lubricant composition is matched to that of each other phase to make the composition clear or translucent. The compositions are highly lubricious, non-staining, and easily washable.

22 Claims, 1 Drawing Sheet

(51) Int. Cl.
*A61K 31/74* (2006.01)
*A61F 6/04* (2006.01)
*A61K 8/34* (2006.01)
*A61K 8/37* (2006.01)
*A61K 8/49* (2006.01)
*A61K 8/81* (2006.01)
*A61K 8/891* (2006.01)
*A61Q 9/02* (2006.01)
*A61Q 19/00* (2006.01)

(56) References Cited

U.S. PATENT DOCUMENTS

| | | |
|---|---|---|
| 5,002,974 A | 3/1991 | Geria |
| 5,137,032 A | 8/1992 | Harmon |
| 5,885,591 A | 3/1999 | Ahmad et al. |
| 5,925,338 A | 7/1999 | Karassik et al. |
| 6,139,848 A | 10/2000 | Ahmad et al. |
| 7,005,408 B2 | 2/2006 | Ahmad et al. |
| 7,285,517 B2 | 10/2007 | Ahmad et al. |
| 7,405,186 B2 | 7/2008 | Harrison |
| 2006/0159645 A1 | 7/2006 | Miller et al. |
| 2006/0217272 A1 | 9/2006 | Harrison |
| 2006/0246027 A1 | 11/2006 | Tanner |
| 2008/0050398 A1 | 2/2008 | Bockmuehl et al. |
| 2008/0248981 A1 | 10/2008 | Matsui et al. |

OTHER PUBLICATIONS

Fevola et al., "Getting Intimate with Polymers Lubricants", Cosmetics & Toiletries® magazine, vol. 123, No. 6 pp. 59-68 Jun. 2008.
International Search Report and Written Opinion dated Jan. 11, 2010 in related PCT Application No. PCT/US09/06003, filed Nov. 6, 2009.
USPTO Office Action dated May 5, 2015 in U.S. Appl. No. 12/586,198, filed Sep. 18, 2009.
USPTO Office Action dated Oct. 1, 2014 in U.S. Appl. No. 12/586,198, filed Sep. 18, 2009.
USPTO Office Action dated Jan. 24, 2014 in U.S. Appl. No. 12/586,198, filed Sep. 18, 2009.
USPTO Office Action dated Oct. 11, 2013 in U.S. Appl. No. 12/586,198, filed Sep. 18, 2009.
USPTO Office Action dated May 21, 2013, in U.S. Appl. No. 12/586,198, filed Sep. 18, 2009.
USPTO Office Action dated Mar. 4, 2013, in U.S. Appl. No. 12/586,198, filed Sep. 18, 2009.
USPTO Office Action dated Oct. 3, 2012, in U.S. Appl. No. 12/586,198, filed Sep. 18, 2009.
USPTO Office Action dated Aug. 1, 2012, in U.S. Appl. No. 12/586,198, filed Sep. 18, 2009.

CLEAR, WASHABLE LUBRICANT COMPOSITIONS AND METHODS OF MAKING SAME

This patent application is a continuation-in-part of U.S. patent application Ser. No. 12/586,198, filed Sep. 18, 2009, which claimed priority under 35 USC §119(e) to Provisional Patent Applications Ser. No. 61/113,623, filed Nov. 12, 2008 and Ser. No. 61/200,290, filed Nov. 26, 2008, the disclosure of each of which is hereby incorporated by reference herein in its entirety.

BACKGROUND OF THE INVENTION

The present invention relates to clear washable bi- or multiphasic lubricant compositions, including personal lubricants, skin conditioners, shaving fluids, and methods for their manufacture and use. Such lubricant compositions are preferably silicone-containing, substantially water-soluble, clear, and generally maintain their lubricity longer than purely water-soluble lubricant, skin conditioning, and shaving compositions of the prior art lacking a silicone component. In certain embodiments the present invention includes condom products including the lubricant compositions of the present invention, and methods of making such condom products. In one particular aspect, the substantially water-soluble, clear, multi-phasic lubricant compositions of the present invention are self-warming lubricant compositions, for example, self-warming personal lubricant compositions, condom products including condoms lubricated with warming lubricant compositions, and method of making such condom products.

Lubrication can be defined as the separation of moving surfaces to prevent them from coming into direct contact with each other (or to reduce the amount of such friction); this tends to prevent or lessen wear and irritation between the surfaces.

Personal lubricants, for example, in the form of water-soluble pourable liquids, water-soluble pourable low viscosity thixotropic gels, water-soluble jellies and the like, are known and are useful for providing lubricity to various parts of the human body, for example, to mucous membranes, such as the oral, rectal, vaginal and other mucosa. For example, see Ahmad et al U.S. Pat. No. 5,885,591, the disclosure of which is incorporated in its entirety herein by reference. Certain such lubricants have been proposed which may generate heat or warming when placed in contact with the human body. See also, Harrison, J., U.S. patent application Ser. No. 11/089,953, published as U.S. Patent Publication 2006/0217272 A1.

Additional personal lubricants have been discussed in e.g., Ahmad et al., U.S. Pat. No. 6,139,848, Ahmad et al., U.S. Pat. No. 7,005,408, Ahmad et al., U.S. Pat. No. 7,285,517, and Harrison, U.S. Pat. No. 7,405,186. These are water-soluble lubricants lacking a silicone component. Some water-soluble lubricants may be tacky and lack a sufficiently high degree of lubricity.

On the other hand, silicone lubricants offer superior lubrication, but generally stain fabrics such as cotton, polyester or satin, can feel greasy and can be difficult to clean up. Silicone and water-soluble phases are immiscible. Therefore an emulsion is necessary to take advantage of the combination of these phases.

Generally emulsions between two immiscible substances are substantially opaque "white" creams due to the admixture of droplets of, for example, oil (such as silicone oil) and of the aqueous phase, wherein the refractive indices of the immiscible phases are different. However, opaque or translucent personal lubricants, particularly those used as sexual lubricants, may appear used, and are therefore generally considered aesthetically unpleasing and may be commercially unsuccessful because of this, despite their physical properties.

Clarification of cosmetics has generally involved using one of two possible approaches: a) the formation of microemulsions or b) matching of refractive indices. See e.g., Sun et al., J. COSMET. Sci. 56, 253-265 (July/August 2005). The formation of microemsulsions generally involves the use of high concentrations of emulsifiers to compete for limited amounts of an oil phase; this force the droplet size to be very small. When the droplet size is less than the wavelength of light, the emulsion will appear clear.

When using the technique of refractive index matching to clarify a mixture of immiscible liquids, generally the formulation is determined empirically and the methodology used in one instance is often not generally applicable, for example, to all or even most formulations. See id. In one reference, an anti-perspirant composition is made using silicone oil and an aqueous liquid. However, this reference contains no methodology, theoretic basis, or even examples of refractive indices. See Karassik et al., U.S. Pat. No. 5,925,338.

Silicone personal lubricants are described in Fevola et al., Cosmetics and Toiletries, 123:6, 59-68 (June 2008). Such personal lubricants are described as being very lubricious, but clean-up is difficult since these personal lubricants are water insoluble.

Lubrication can also be an advantageous property of shaving fluids. The greater the degree of lubrication while shaving, the lesser the tendency for the razor to irritate the skin. The increased lubricity of the present compositions, combined with their clarity or translucence can add to the aesthetic appeal and marketability of such a composition as well.

Personal lubricants, for example, in the form of pourable liquids, pourable low viscosity thixotropic gels, jellies and the like, are known and are useful for providing lubricity to various parts of the human body, for example, to mucous membranes, such as the oral, rectal, vaginal and the like mucosa. For example, see Ahmad et al U.S. Pat. No. 5,885,591, the disclosure of which is incorporated in its entirety herein by reference. Certain such lubricants have been proposed which generate heat or warming when placed in contact with the human body.

Using condoms lubricated with clear lubricants has also been proposed. Producing such lubricated condoms is somewhat challenging, particularly if the lubricant is to be applied both inside and on the outside of the condom. Conventional machinery used in condom manufacture mandates that the lubricant composition has relatively tight specifications, for example, in terms of viscosity, tackiness and stringiness, as well as providing the desired degree of lubricity.

Also lubrication in a skin conditioner, particularly skin conditioners containing silicone, can give a smooth, silky feeling to dry, chapped skin. However, a single-phase silicone skin conditioner can be difficult to wash away. Moreover, an opaque or cloudy skin conditioner is unappealing when it is being used, as it may be visible as a layer on the skin.

There continues to be a need for new substantially clear personal lubricant, skin conditioner and shaving fluid compositions having increased lubricity, a smooth, non-tacky feel, and good longevity, which can be cleaned relatively easily and which does not stain clothing, as well as for condom products including personal lubricants and methods of making such materials, for example, new lubricant compositions, condom products including clear, non-staining lubricants and methods of making such condom products.

SUMMARY OF THE INVENTION

New lubricant compositions, condom products containing such lubricants and methods of making such condom and lubricant products have been discovered. The present lubricant compositions have a unique combination of desirable characteristics, being, for example, substantially clear or translucent, easily cleaned, substantially non-staining compositions having excellent lubricity, which have reduced tackiness relative to one or more prior art body lubricants. In addition, the present compositions can have relatively widely varying chemical compositions, and therefore, can be employed in many applications, for example, as stand alone lubricant products, for example, personal lubricant products, in combination with one or more medications, such as anti-fungal agents and the like, and/or in combination with devices, such as condoms and the like. In one embodiment, the present lubricant compositions are particularly useful to provide lubrication for condoms, for example, in packaged condom products. Also, such compositions may find uses as medical lubricants, for example, gynecological or surgical lubricants, as shaving fluid products, and as skin conditioning products. It will be understood that the term "lubricant compositions" or "lubricant(s)" as used in this application, shall include shaving gels and fluids, skin conditioners, and any other suitable product unless otherwise expressly indicated or obvious from the context.

An important aspect of the present invention is the ability to form a clear composition comprising two or more immiscible phases, for example, a silicone oil phase and an aqueous or hydrophilic component. The lubricant compositions made using such methods are effective and enjoyable in use, whether as a stand-alone product or in combination with one or more medications and/or devices, and are substantially non-staining and/or easy to wash from clothing or skin. In certain embodiments, the compositions of the present invention may be formulated as a self-warming lubricant formulation.

In one broad aspect of the present invention, the present lubricant compositions comprise a lubricant comprising a silicone component, water (except in self-warming formulations, which should be maintained as substantially anhydrous), a hydrophilic component, which may comprise an alkylene glycol component (such as, without limitation, a ethylene, propylene, hexylene, or butylene glycol component) or a polyalkylene glycol component (such as a polyethylene glycol component, a polypropylene glycol component, a mixed polyalkylene glycol component, or a mixture of two or more of these), and a small amount of an emulsifier. Such a composition will possess a high degree of clarity/translucency when the refractive indices of the silicone component and the aqueous phase are matched. Thus, this composition is aesthetically pleasing and desirable over white or translucent lubricants, particularly as a personal lubricant. Additionally, such lubricants have a smoothness, lubricity, and longevity in use that is vastly superior to purely aqueous-based lubricants, and yet can be washed from fabric easily, and without staining, unlike purely silicone-based lubricants.

The compositions are preferably substantially clear or transparent. In one useful embodiment, the present compositions may be in the form of massage lubricants that are very effective when used on the human body). In additional, non-exclusive, embodiments the lubricants may be sexual lubricants, or may be surgical lubricants.

Since the present lubricants may be pourable liquids, clear lotions, or gels, the viscosities of the present compositions can be varied over a relatively broad range depending, for example, on the particular application for which the composition is to be used. For example, the present compositions can have a viscosity, at 25° C., in a range of about 50 cps (centipoise) or less to about 5000 cps or about 10,000 cps or more. In situations where the lubricant composition is designed for use as a stand alone personal lubricant or as a lubricant for a condom, for example, a packaged lubricated condom product, viscosities (at 25° C.) of less than about 500 cps or less than about 1000 cps or less than about 2000 cps, for example, in a range of about 50 cps or about 100 cps to less than about 500 cps or less than about 1000 cps or less than about 2000 cps are advantageously useful.

However, while the present compositions may be formulated as, for example, a pourable liquid or a liquid-like gel, as currently preferred the compositions of the present invention are formulated as a stiff gel, having a viscosity in the range of about 45,000 cps to about 60,000 cps.

The viscosity of the compositions of the claimed invention may be adjusted as desired. Thus, a viscosity may be altered, at least in part, by increasing or decreasing the molecular weight of the silicone or hydrophilic components used. Additionally, the compositions may be formulated to change phases due to the decrease in viscosity when warmed to body temperature. Thus, for example, a gel may become a liquid when warmed by body heat.

Preferably, although not invariably, the silicone component of the present compositions often comprises a dimethacone (trimethyl siloxane-terminated polydimethylsiloxane) or phenyltrimethicone component. Additional or alternative silicones may be present; these additional or alternative silicone components may include one or more of the following: a dimethiconol (hydroxy-terminated polydimethylsiloxane) component, a cyclopentasiloxane component, a dimethicone/vinyl dimethicone cross-polymer component. For example, a silicone component may comprise a D5 cyclic or small linear dimethicone and/or a disiloxanevinyl cross polymer.

Additionally, the present compositions comprise a hydrophilic component. The hydrophilic component usually contains a water-soluble polymer, such as, without limitation, an acrylate component. In certain embodiments the hydrophilic component may comprise water; in other embodiments it may be substantially anhydrous. The acrylate component may include one or more of the following: a polyacrylamide component, an acrylamide/sodium acryloyl dimethyl taurate copolymer component, a hydroxyethyl acrylate/sodium acryloyl dimethyl taurate copolymer component, a polyacrylate-X component, and/or a sodium acrylate/sodium acryloyl dimethyl taurate copolymer component.

In other embodiments the hydrophilic component may alternatively or additionally comprise an alkylene glycol, such as propylene glycol or butylene glycol. In the same or other embodiments, the hydrophilic component may comprise a hydrophilic polyalkylene glycol component, such as a polyethylene glycol or a polypropylene glycol. When formulating the compositions of the present invention, this portion of the hydrophilic component may be separately added to other portions of the hydrophilic component, and/or may be added to adjust the refractive index if necessary as a last step in the formulation process.

Preferably, the present lubricant compositions are substantially clear or substantially transparent at temperatures in a range of about 20° C. to about 40° C., for example, 25° C. or about 37° C.

In keeping with the present invention, the inventors have recognized that the reason most emulsions are white or translucent rather than substantially clear is due to differences in the refractive indices of at least two immiscible phases of the emulsion. By contrast, when the refractive indices of the two or more phases are identical, or substantially identical, the emulsion appears clear.

The refractive index (n) is a dimensionless term specific for a given medium comprising a ratio of the speed of light in a vacuum (c) and the speed of light through the medium at issue (v). Thus, the refractive index of a medium is expressed as n=c/v according to Snell's law. The refractive index is conventionally determined at 25° C. The refractive index of water is 1.3330, while the refractive index of, for example, a preparation of cyclodimethicone, phenyltrimethicone and dimethicone (sold as Gelaid 5565 by Chemsil Silicones Inc.) is 1.4015.

If the refractive indices of two clear compositions are made to equal each other, then the angle of refraction of light through the media will also be equal, and an emulsion made from each of these separately clear compositions will also be clear.

If several miscible solutes are mixed together to form a clear, homogeneous liquid, the refractive indices of each such ingredient can be used to calculate the refractive index of the final solution. Usually (but not always) the calculated value of the mixture's refractive index ("RI") will agree with the experimentally determined value quite closely. Thus, in such cases, if W equals the weight of each component and n is the RI of each component, the RI of the mixture can be determined using the following equations:

$$RI_{mix} = [W_1 \times n_1 + W_2 \times n_2 + \ldots W_n \times n_n]/W_T \quad (1)$$

where $W_T = W_1 + W_2 + \ldots W_n$,
which can be simplified to:

$$RI_{mix} = [\Sigma(W_i \times n_i)]/[\Sigma W_i] \quad (2)$$

Thus, it is possible to separately mix ingredients of each of two immiscible phases, for example, hydrophilic and silicone soluble ingredients, to have substantially equal RIs such that upon combining the phases the resulting mixture or emulsion is clear or opalescent. However, a number of assumptions must be assumed in order for this principle to hold true. These assumptions include: that no chemical reaction occurs between ingredients in either immiscible phase, that the ingredients (such as solvent and solutes) in one phase are not soluble in the other phase (and that any emulsifier should remain at the interface of its phase, and should not permeate the other phase), and that the emulsions be made at room temperature, since RI values are temperature-dependent.

For personal lubricants, including those used in conjunction with condom products, it is important that all the ingredients (including the silicone ingredients) be substantially non-toxic and non-irritating to the skin.

As indicated above, in making the various phases, there may be some variation from the calculated RI values. The variation will generally be greater for the aqueous phase than for the silicone, where all the values are quite close together to begin with. To adjust the RI values of the hydrophilic and the silicone component, water can be used to lower the RI values and various alkylene glycols or polyalkylene glycols can be used to raise the refractive index.

Examples of alkylene glycols and their derivatives that can be used to adjust the RI values of a hydrophilic phase in the present compositions include, without limitation, propylene glycol, butylene glycol, hexylene glycol, glycerin and glycereth-7. Additionally, polyalkylene glycols, for example, PEG 200 (polyethylene glycol with an average molecular weight of 200 Daltons) or PEG 400 (with an average molecular weight of 400 Daltons) may be used to adjust the RI values. The person of ordinary skill in the art is aware that various forms (e.g., straight chain or branched) of these compounds may be used. When aqueous concentration is plotted against RI, the largest deviation from the predicted RI values among selected alkylene glycols are seen using glycerin (negative variation) and hexylene glycol (positive deviation); all deviations are concentration dependent. Propylene glycol, butylene glycol and hexylene glycol all show positive deviation from the calculated values.

One of the more efficient methods of raising the refractive index of the lubricant composition of the present invention is to use a combination of hexylene glycol in combination with glycerin, glyceryth-7, or butylene glycol or propylene glycol. For example, the hexylene glycol may be in the range from about 20% to about 30% by weight.

Another ingredient of the present lubricant formulations is one or more hydrophilic component. Such hydrophilic components generally comprise polymeric components lending a gelling ability or lubricity to the composition, as well as surfactants and/or emulsifiers. Thus, such components may include, without limitation, polyacrylamide, isoparaffin, lauryth-7 (these ingredients together are contained in a product named Seppic® Gel 305); acrylamide/sodium acryloyl dimethyltaurate copolymer/isohexadecane/polysorbate 80 (these ingredients together are contained in a product named Simulgel® 600)(gelling agent); polyacrylate-X/Isohexadecane/polysorbate 60 (these ingredients together are contained in a product named Simulgel® SMS-88); sodium acrylate/acryloyl dimethyltaurate copolymer/Isohexadecane/polysorbate 80 ((these ingredients together are contained in a product named Simulgel® EG). hydroxyethyl acrylate/sodium acryloyl dimethyltaurate compolymer/isohexadecane/polysorbate 80 (these ingredients together are contained in a product named Simulgel® NS).

In other embodiments, the hydrophilic component may comprise a polyalkylene glycol component, for example, a substantially anhydrous preparation of a polyalkylene glycol, which may be added at the same or a different time as the remainder of the hydrophilic component. If present, the polyalkylene glycol component may, but need not, comprise two or more populations of polyalkylene glycol, such as two or more preparations having different average molecular weights. The polyalkylene glycols of the present invention are soluble in water, and may comprise polyethylene glycol, polypropylene glycol, copolymers of these, and the like. Preferably the polyalkylene glycol is a polyethylene glycol.

In certain embodiments, see Harrison et al., U.S. Pat. No. 7,405,186, the disclosure of which is hereby incorporated by reference herein in its entirety, substantially anhydrous liquids containing polyalkylene glycol can be used to make self-warming fluids, such as self-warming personal lubricants.

In such embodiments containing two or more polyalkylene preparations having different average molecular weights, the weight ratio of a first polyalkylene glycol component portion to a second polyalkylene glycol portion may vary over a relatively wide range, for example, from about 0.1 to about 10. Such ratio may be less than about 7 or less than about 3 or less than about 1.3.

The polyalkylene glycol component, for example (without limitation), the first and second polyalkylene glycol component portions combined or together, may be at least about 70% by weight or at least about 80% by weight or at least about 90% by weight of the hydrophilic component of the present composition. The compositions of this embodiment of the invention preferably may have an enhanced ability to generate heat when placed in contact with water or when placed in contact with a mucous membrane of a living human, relative to a similar or substantially identical composition containing a reduced amount, for example, at least 5% by weight less, of the polyalkylene glycol component in the hydrophilic component.

The polyalkylene glycol components, and component portions, may have molecular weights varying over relatively wide ranges, for example, in a range of about 100 or about 150 or about 200 or about 300 or about 400 to about 500 or about 600 or about 800 or about 1000 or about 3000 or about 5000 or more. This disclosure is intended to encompass and specifically, although not exclusively, disclose every range of molecular weights between 100 Daltons and 5000 Daltons. In one embodiment, without limitation, the first polyalkylene, for example, polyethylene, glycol component portion preferably has a molecular weight in a range of about 350 to about 450. The second polyalkylene, for example, polyethylene, glycol component portion, if present, preferably has a molecular weight in a range of about 150 to about 250.

The hydrophilic component may additionally or alternatively comprise polyvinyl pyrrolidine (PVP) components. These water-soluble compounds increase the viscosity of the lubricant compositions. Additionally, different preparations of PVP components may be used, such as preparations have different average molecular weights. Other hydrophilic agents may include, without limitation, polyvinyl alcohol and glycerin.

The present compositions will often, but not invariably, contain a preservative component. Such a component will comprise any suitable and effective preservative that is generally regarded as safe. The compositions of the present invention preferably contain preservative components such as Glydant Plus® (DMDM hydantoin (1,3-bis(hydroxymethyl)-5,5-dimethylimidazolidine-2,4-dione) and iodopropynyl butylcarbamate) or any other cosmetically or pharmaceutically safe and effective preservative component. For example, and without limitation, other preservative components may comprise methylparaben, benzoic acid, sorbic acid, gallic acid, propylparaben and the like and mixtures thereof. The preservative component may be present, if at all, in the present compositions in an amount in a range of about 0.01% or less to about 0.5% or more by weight, depending on the specific preservative activity of the preservative. In certain embodiments, a preservative may be chosen to be soluble in each of the immiscible phases. In other embodiments, more than one preservative may be used, preferably with at least one preservative soluble in two or more, or each, of the immiscible phases of the composition.

In certain aspects of the invention, the present compositions may be used in conjunction with condoms, for example, packaged condom products. Such products may comprise: a condom, for example, comprising latex, or another polymeric "skin", one or more other naturally occurring materials, such as animal intestine material and the like, one or more other synthetic materials, such as synthetic polymeric materials and the like, and mixtures thereof; a lubricant composition, comprising the compositions described elsewhere in this patent specification; and a package containing the condom and the lubricant composition. The package, containing the condom and the lubricant composition, is sealed for transportation and storage prior to use. In one embodiment, the condom includes an inner wall and an opposing outer wall both of which are in contact with the lubricant composition. The package may be made of any suitable material or combination of materials. In one embodiment, the package comprises at least one of metal foil and polymeric packaging material.

In a further broad aspect of the invention, methods of making or manufacturing condom products are provided. Such methods comprise: providing a condom; contacting the condom with the bi- or multiphasic, silicone-containing lubricant composition described elsewhere herein, in an amount effective to lubricate the condom for use; placing the lubricated condom in a package.

In embodiments of the bi- or multiphasic lubricant in which the lubricant is self-warming, the condom and lubricant are sealed in a package, thereby forming a sealed package in which the condom and bi- or multiphasic lubricant composition are maintained as substantially anhydrous.

Each and every feature described herein, and each and every combination of two or more of such features, is included within the scope of the present invention provided that the features included in such a combination are not mutually inconsistent.

These and other aspects and advantages of the present invention will become apparent when considered in light of the following detailed description and claims.

DETAILED DESCRIPTION

The present invention is drawn to new multi-phasic lubricant compositions, including, but not limited to, new personal lubricants, shaving aids (including preshaves), new condom products, substantially non-staining massage lubricants, and new methods of making personal lubricants and condom products.

The present lubricant composition comprises at least two substantially immiscible phases comprising:
 a) a hydrophilic component, which may in certain embodiments comprise an aqueous phase, and in other embodiments lack substantial amounts of water, and
 b) a silicone component, such as a phase containing a silicone oil,
 wherein the composition is substantially clear or transparent.

Preferably, the respective refractive indices of the silicone and hydrophilic components of the composition are made to match within about 0.0001 unit, or within about 0.0005 units, or within about 0.001 units, or within about 0.005 units or within about 0.01 units or less. Alternatively, the refractive indices of the immiscible components of the composition are made to match within about 1% or about 2% or within about 4% or within about 8% or within about 10% or within about 15% or within about 20% of each other. In another alternative embodiment, the refractive indices of the immiscible components of the composition are made to match sufficiently so as to render substantially undetectable an interface between the phases under ordinary lighting, or so as to render the composition substantially clear or translucent.

The lubricant compositions of the present invention are substantially clear, transparent or translucent (such as opalescent), and a relatively wide range of desired viscosities can be easily obtained. Indeed, one of the advantages of the present invention is the ability to formulate compositions of various viscosities without causing substantial tackiness and/or stringiness. The present compositions may be in the form of a liquid, a semi-solid (such as a gel), or a solid depending upon the particular intended use thereof. The present compositions may be formulated as syrupy liquid-gels pourable gels or thick jellies or as pourable liquids. Preferably, the viscosities are in a range of about 50 cps or about 100 cps to less than about 500 cps or less than about 1000 cps or less than about 2000 cps. However, as noted above, viscosities in the present compositions may range from about 1000 cps to about 10,000 cps for gel, and from 60,000 cps to about 500,000 cps or more for the jellies. In currently less preferred embodiments the present compositions may also be formulated into soft or hard gelatin capsules, suppositories, and/or impregnated into fabrics or polymers.

In preferred embodiments the lubricant composition is effective as a personal lubricant and is therefore substantially non-irritating to skin and oral, anal, penile, and vaginal mucosa.

In another embodiment the present invention may comprise a method of making a substantially clear or translucent lubricant composition, preferably a personal lubricant composition, containing at least two substantially immiscible phases comprising:
  a) a hydrophilic component, which may in certain embodiments comprise an aqueous phase, and in other embodiments lack substantial amounts of water, and
  b) a silicone component, such as a phase containing silicone oil,
  wherein the refractive indices of the immiscible phases are substantially identical.

"Substantially identical" refractive indices are respective refractive indices of the silicone and hydrophilic components of the composition within about 0.0001 unit, or within about 0.0005 units, or within about 0.001 units, or within about 0.005 units or within about 0.01 units. Alternatively, substantially identical refractive indices of the immiscible components of the composition match within about 1% or about 2% or within about 4% or within about 8% or within about 10% or within about 15% or within about 20% of each other.

Lacking "substantial amounts of water" and "substantially anhydrous", as used in this application, means having either no detectable water, or so little water that the heat of dilution of water-soluble components of the composition is affected by no more than 10% by the presence of water.

In another embodiment of the present invention, the present invention is directed to a self-warming bi- or multiphasic lubricant composition that is washable, clear or translucent, and exhibits the high degree of lubricity characteristic of silicone-based lubricants.

These self-warming compositions are dual or multiphase compositions comprising initially substantially anhydrous mixtures of a hydrophilic polyalkylene glycol component and hydrophobic silicone-containing lubricity component.

In certain of these embodiments, the polyalkylene glycol component comprises for example, a substantially anhydrous preparation of a polyalkylene glycol. The polyalkylene glycol component may, but need not, comprise two or more populations of polyalkylene glycol, such as two or more preparations having different average molecular weights. Preferably the polyalkylene glycol is a polyethylene glycol. See Harrison et al., U.S. Pat. No. 7,405,186, the disclosure of which is hereby incorporated by reference herein in its entirety, for a description of how substantially anhydrous liquids containing polyalkylene glycol can be used to make self-warming fluids, such as self-warming personal lubricants.

In certain preferred embodiments, the composition may contain more than one polyalkylene glycol component portion. In such compositions, the weight ratio of a first polyalkylene glycol component portion to a second polyalkylene glycol portion may vary over a relatively wide range, for example, from about 0.1 to about 10. Such ratio may be less than about 7 or less than about 3 or less than about 1.3.

When used in a self warming composition, the polyalkylene glycol component, whether a single portion alone or two or more polyalkylene glycol component portions combined or together, may be at least about 70% by weight or at least about 80% by weight or at least about 90% by weight of the hydrophilic component of the present composition. The compositions of this embodiment of the invention preferably have an enhanced ability to generate heat when placed in contact with water or when placed in contact with a mucous membrane of a living human, relative to a similar or substantially identical composition containing a reduced amount, for example, at least 5% by weight less, of the polyalkylene glycol component in the hydrophilic component.

The polyalkylene glycol components, and component portions, may have molecular weights varying over relatively wide ranges, for example, in a range of about 100 or about 150 to about 1000 or about 3000 or about 5000 or more. Preferred average molecular weights include about 400 Daltons. In one embodiment, a first polyalkylene glycol component portion, for example, polyethylene glycol component portion, preferably has a molecular weight in a range of about 350 to about 450. If present the second polyalkylene glycol component portion, for example, polyethylene glycol component portion, preferably has a molecular weight in a range of about 150 to about 250.

The hydrophobic silicone component of the present compositions often comprises a dimethacone (trimethyl siloxane-terminated polydimethylsiloxane) and/or phenyltrimethicone component. Additional or alternative silicones may be present; these additional or alternative silicone components may include one or more of the following: a dimethiconol (hydroxy-terminated polydimethylsiloxane) component, a cyclopentylsiloxane component, a dimethicone/vinyl dimethicone cross-polymer component. For example, a silicone component may be a D5 cyclic or small linear dimethicone, disiloxane vinyl cross polymer.

In certain aspects, the present lubricant compositions may comprise a polyalkylene glycol component. As discussed above, the polyalkylene glycol component may be present as an agent in a substantially anhydrous composition, providing an exothermic heat or dilution when mixed with water, such as a moist skin or mucosal membrane surface. The polyalkylene glycol component may also be present in a composition containing water in a hydrophilic phase; an example of such a composition is provided above.

The polyalkylene glycol components may include polyalkylene glycols, polyalkylene glycol ethers, for example, polyalkylene glycol stearates, oleates, cocoates, and the like and mixtures thereof. Advantageously, the polyalkylene glycol component is selected from polyethylene glycols (hereinafter referred to as PEG's), polypropylene glycols, polypropylene glycol ethers, polyethylene glycol ethers, and the like and mixtures thereof. PEGylated compounds, such as peptide or protein derivatives obtained by PEGylation reactions may also be used. In addition, block copolymers of PEG's may be used, such as (ethyleneglycol)-block-poly(propyleneglycol)-block(polyethylene glycol), poly(ethylene glycol-propylene glycol) (random copolymer) and the like and mixtures thereof. The compositions of this invention comprise at least about 25%, or about 30%, or about 35%, or about 40% or about 45% or about 50% by weight of the polyalkylene glycol component, more preferably at least about 35% by weight of the composition.

It will be understood that, due to the stoichiometric nature of osmotic forces, the difference in the osmolality of two otherwise identical lubricants of equal viscosity will be greater if one uses a lower molecular weight polymer versus the same weight percentage of a higher molecular weight polymer. Thus, all other things being equal the substitution of a lower molecular weight component, (for example, a glycol like propylene glycol) with the same weight percentage of a higher molecular weight component (such as a polyalkylene glycol like PEG 400) will generally result in a lubricant that is less drying to the skin, since it has a lower osmotic pressure. Thus, it may be desirable to consider osmolality when choosing the ingredients for the formula of a specific lubricant.

In a useful embodiment, particularly useful for self-warming lubricant compositions, the polyalkylene glycol component may be, but need not be, present in two or more different portions. In such a case, each portion may have a different average molecular weight. For example, in one embodiment the lubricant compositions of the present invention comprise a first polyalkylene glycol component portion having a first molecular weight and a second polyalkylene glycol component portion having a second molecular weight reduced relative to the first molecular weight. For self warming compositions it has been found that controlling the molecular weight of the polyalkylene glycol component and maintaining a relatively high concentration of the polyalkylene glycol component are effective in providing the present lubricant compositions with a substantially advantageous combination of benefits, particularly if the lubricant composition is to be a self-warming composition. In such compositions, for example, the presence of relatively high proportions of the anhydrous polyalkylene glycol component provides an increased or enhanced degree of warming, for example, relative to similar compositions which have less than about 50% by weight or less than about 30% by weight of the polyalkylene glycol component.

When such compositions are mixed with a silicone component, and the refractive indices of the silicone and hydrophilic components matched, the composition becomes relatively clear, washable, and lubricious.

For all of the present compositions a wide range of desired viscosities can be easily obtained; the mixture of immiscible silicone and hydrophilic components permits the making of formulations having a relatively low coefficient of friction, which are not tacky and which wash well from skin and fabric compared to strictly silicone lubricants. Hydrophilic and silicone components having a given molecular weight tend to be more viscous than those possessing the same subunits but having a lower molecular weight. Therefore, a composition of the present invention may easily be made to possess a desired viscosity.

Thus, the present compositions may be made to be in the form of a liquid, a semi-solid, or a solid depending upon the particular intended use thereof. The present compositions may be formulated as liquid gels, pourable gels or thick jellies or as pourable liquids. Preferably, the viscosities are in a range of about 50 cps or about 100 cps to less than about 500 cps or less than about 1000 cps or less than about 2000 cps. However, as noted above, viscosities in the present compositions may range from about 1000 cps to about 10,000 cps for gel, and from 60,000 cps to about 500,000 cps or more for the jellies. If desired the present compositions may also be formulated into soft or hard gelatin capsules, suppositories and impregnated into fabrics or polymers.

A preservative component may be added to guard against microbial growth. The preservative component may be selected from preservatives known to those of skill in the art, including, but not limited to, one or more of the following: Glydant Plus® (containing DMDM hydrantoin and iodopropynyl butylcarbamate), methylparaben, benzoic acid, sorbic acid, gallic acid, propylparaben and the like and mixtures thereof. The preservative component may be present, if at all, in the present compositions in an amount in a range of about 0.01% or less to about 0.5% or more by weight.

In certain aspects of the invention fragrances, colors, and/or flavors may be added to the lubricant compositions of the present invention to enhance the subjects' pleasure when using the lubricant. For example, such fragrances may include, without limitation, a citrus (e.g., orange, lime, grapefruit), a melon (e.g., watermelon or honeydew), a berry fragrance, frankincense, myrrh, mango, coconut, vanilla, cucumber, patchouli, and the like.

Similarly, the lubricant may be made using a flavor, for example (if a fragrance is also used) a corresponding flavor, such as, without limitation, a citrus (e.g., orange, lemon, lime, grapefruit), a melon (e.g., watermelon or honeydew), a berry, other fruits or spices (such as mango, coconut, vanilla), and the like. Sweeteners may also be used, such as sugars, saccharin, aspartame, sucralose, neotame, and acesulfame potassium.

Notwithstanding the above, in other embodiments the invention of the present application may be made to be odorless and/or tasteless. An unflavored or unscented lubricant is not only is favored by many people, but may tend to be less allergenic or irritating to these having sensitive skin.

The compositions of the present invention may also be useful as massage liquids, gels and creams. The silicone component may be useful as a skin conditioner.

Certain of the compositions of this invention may be used as personal lubricants that convey a feeling of warmth. The feeling of warmth generated by the compositions of this invention is soothing to the skin or mucous membranes where they are applied. The compositions of this embodiment of the invention may convey a feeling of warmth when applied, for example, to vaginal, anal, or oral mucosa. Such warming effect has been found to enhance intimacy and increase pleasure during intimate activities.

In addition to their use as lubricants per se, the present compositions may be used to relieve vaginal dryness or dry mouth, to moisturize skin, to provide an ameliorating effect for frostbite or extremities overexposed to the cold and the like applications. The present compositions may be useful for treating conditions of infection on the skin or mucosa while soothing the area of infection.

The present compositions may also be used as vehicles to deliver medication or other treatment agents to biomembranes including, but not limited to, hormones, antimicrobials, antibacterials, antibiotics, non-steroidal anti-inflammatory agents, spermicides, immunodilators, anaesthetics, plant extracts, vitamins, corticosteroids or antifungal agents and the like and mixtures thereof.

Antifungal agents are preferably azoles or imidazoles, including by not limited to, miconazole, econazole, terconazole, saperconazole, itraconazole, butaconazole, clotrimazole, tioconazole, fluconazole and ketocanazole, vericonazole, fenticonazole, sertaconazole, posaconazole, bifonazole, oxiconazole, sulconazole, elubio, vorconazole, isoconazole, flutimazole, tioconazole and their pharmaceutically acceptable salts and the like. Other antifungal agents may include an allylamine or one from other chemical families, including but not limited to, ternafine, naftifine, amorolfine, butenafine, ciclopirox, griseofulvin, undecyclenic acid, haloprogin, tolnaftate, nystatin, iodine, rilopirox, BAY 108888, purpuromycin and their pharmaceutically acceptable salts.

The present compositions, for example, for vulvovaginal or other mucosal use, may include one or more antibiotics including, but not limited to, metronidazole, clindamycin, tinidazole, ornidazole, secnidazole, refaximin, trospectomycin, purpuromycin and their pharmaceutically acceptable salts and the like and mixtures thereof.

The present compositions, for example, for vulvovaginal or other mucosal use, may include one or more antiviral agents including but are not limited to, immunomodulators, more preferably imiquimod, derivatives thereof, podofilox, podophyllin, interferon alpha, reticolos, cidofovir, nonoxynol-9, pharmaceutically acceptable salts thereof and the like and mixtures thereof.

The present compositions may include one or more spermicides including, but are not limited to, nonoxynol-9, octoxynol-9, dodecaethyleneglycol monolaurate, Laureth 10S, and Methoxypolyoxyethyleneglycol 550 Laurate and the like and mixtures thereof.

The present compositions may include antimicrobial agents, including but are not limited to, chlorohexidine gluconate, sodium polystyrene sulfonate, sodium cellulose sulfate, silver particles of micro- and sub-micrometer sizes, silver salts and other antibacterial agents known to the art and the like and mixtures thereof.

The present compositions may include local anesthetics, including but are not limited to, benzocaine, lidocaine, dibucaine, benzyl alcohol, camphor, resorcinol, menthol and diphenylhydramine hydrochloride and the like and mixtures thereof.

The present compositions may include plant extracts such as aloe, witch hazel, chamomile, hydrogentated soy oil and colloidal oatmeal, vitamins such as vitamin A, D or E and corticosteroids such as hydrocortisone acetate, and the like and mixtures thereof.

The present compositions, for example, for vulvovaginal or other mucosal use, may include one or more hormones for treating a decrease in estrogen secretion in the woman in need of estrogen replacement, such as women with vaginal atrophy. The hormones may include, but are not limited to, estrogen elected from the group consisting of estradiol, estradiol benzoate, estradiol cypionate, estradiol dipropinonate, estradiol enanthate, conjugated estrogen, estriol, estrone, estrone sulfate, ethinyl estradiol, estrofurate, quinestrol and mestranol and the like and mixtures thereof.

The present compositions may contain agents known to those of skill in the art to treat female sexual dysfunction (including different aspects of female sexual dysfunction such as female sexual arousal disorder, hypoactive sexual desire disorder, orgasmic disorder and the like) as well as those that treat dyspareunia and/or vaginismus or vulvodynia and to relieve pain upon intercourse. Such agents include hormones such as estrogen, prostaglandin, testosterone; calcium channel blockers, cholinergic modulators, alpha-adrenergic receptor antagonist, beta-adrenergic receptor agonists, camp-dependent protein kinase activators, superoxide scavengers, potassium channel activators, estrogen-like compounds, testosterone-like compounds, benzodiazepines, adrenergic nerve inhibitors, HMG-COA reductase inhibitors, smooth muscle relaxants, adrenosine receptor modulators and adenylyl cyclase activators. Such agents include phosphodiesterase-5 inhibitors and the like. The present compositions may also contain vasodilators such as methyl nicotinate, histamine hydrochloride and very small non-irritating amounts of methyl salicylate.

The present compositions, for example, for vulvovaginal use, may contain one or more analgesics and/or nonsteroidal anti-inflammatory agents for treating dysmenorrhea or menstrual cramping. The analgesics and nonsteroidal anti-inflammatory agents may include, but are not limited to, aspirin, ibuprofen, indomethacin, phenylbutazone, bromfenac, fenamate, sulidac, nabumetone, ketorolac, and naproxen and the like and mixtures thereof.

The present compositions, for example, for oral, vulvovaginal and/or other mucosal use, may enhance the absorption of active agents from the applied compositions into the mucosal membrane by increasing the composition and mucosal tissue temperature upon contact with the tissue.

The present compositions may be manufactured as a coating of a tampon, or dispersing throughout the absorbent tampon material, or enclosed inside as a core of a tampon.

The present compositions may be applied to the oral, anal, or vaginal mucosal tissues manually or via a swab or vaginal applicator of in any way known to those of ordinary skill in the art.

In one particularly useful aspect of the present invention, the present lubricant compositions may be employed in the manufacture of a packaged condom product.

Such a method of manufacturing a condom product is included within the scope of the present invention and comprises providing a condom, for example a condom which comprises latex. The condom is contacted with a lubricant composition, for example in accordance with the present invention as described elsewhere herein, in an amount effective to lubricate the condom for use. Advantageously, both the inner wall of the condom and the outer wall of the condom are contacted and lubricated with the lubricant composition. The lubricated condom is placed in a package which is thereafter sealed to form a sealed package in which the condom and lubricant composition are substantially anhydrous.

The package is opened to remove the condom, which is then available for use, as desired.

A packaged condom product is also an aspect of the present invention and is included within the scope of the present invention. An example of such a packaged condom product is shown in FIG. 1.

Figure 1:
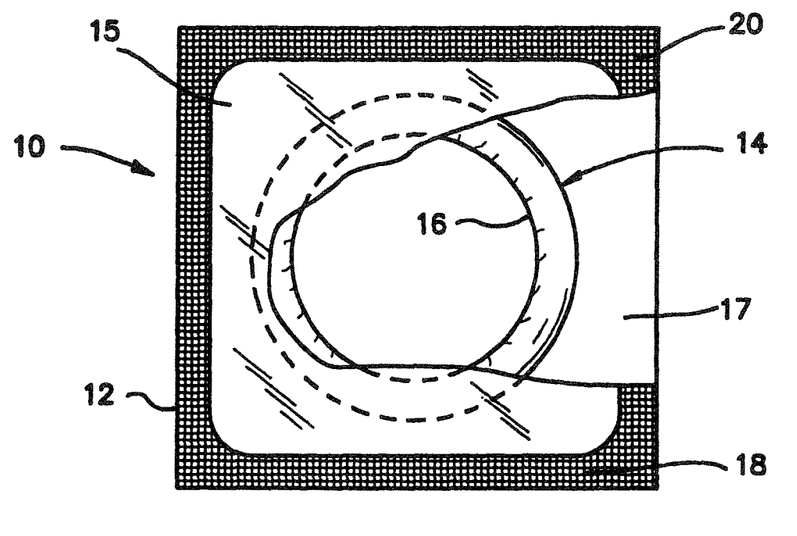
FIG. 1 shows a cutaway drawing of a packaged condom product.

Referring now to FIG. 1, the packaged condom product shown generally at 10 includes a sealed package 12, and a rolled condom 14. The package 12 is made of conventional polymeric packaging material and/or conventional metal foil packaging material.

The inner and outer walls of the condom 14, which is made of latex, are lubricated with a substantially clear lubricant composition in accordance with the present invention. Such lubricant, shown as 16 is advantageously substantially not stringy and has a control degree of tackiness, from the component portions, as described elsewhere herein in the lubricant composition.

The sealed package 12 includes front wall 15, back wall 17 and seals 18 and 20, which together form an outer perimeter region of the package. Either or both of the seals 18, 20 can be compromised to remove the condom from the package 12, for use, as desired.

The packaged condom product 10 is made using conventional condom manufacturing equipment in which the lubricant composition 16 is included with the condom during the normal course of manufacture, for example, in a manner substantially similar to that used to lubricate condoms with conventional condom lubricants.

A further aspect of the invention involves a product for use in preparing the lubricant compositions of the present invention. In this embodiment, one or more portions of the hydrophilic component are pre-mixed with one or more portions of the silicone component. In some embodiments the portions of the hydrophilic component include every element other than a) water and b) a refractive index-adjusting amount of a hydrophilic portion, such as an alkylene glycol or a polyakylene glycol, or a hydrophobic silicone portion. In these embodiments, a pre-mixed composition comprising, for example, a combination of one or more element of the silicone component. An example of such a composition is provided below:

Pre-Mixed Components for Formulating Washable Lubricant Compositions

The hydrophilic components and the hydrophobic components may be separately made, if necessary and mixed. For example, the following composition is made as follows:

Hydrophobic Portions Cyclopentasiloxane (and) Dimethicone/Vinyl Dimethicone Crosspolymer (and) Cyclohexasiloxane.

Hydrophilic Components

Hydroxyethyl Acrylate/Sodium Acryloyl Dimethyl Taurate Copolymer

4% (by weight) of the former is added to 96% (by weight) of the latter, and gently mixed at room temperature until uniform. The resulting composition is an opaque paste ("Paste") having very low toxicity, or dermal irritability characteristics. The Paste can be used as a gelling agent to make clear, refractive index-matched compositions in "cold mix" processes requiring no heat. The product may be formulated with either or both hydrophobic active ingredients or hydrophilic active ingredients, if desired. The viscosity of the paste is from about 22,000 to about 28,000 centipoise.

This Paste may be used in, for example, personal lubricant or hair gel formulations. Prototypes may include, but are not limited to, the following:

| | |
|---|---|
| A. Deionized Water | 30% by weight |
| B. Propylene Glycol | 35% by weight |
| C. PVP/vinyl acetate copolymer | 10% by weight |
| D. Paste | 23% by weight |
| E. Propylene Glycol | 2% by weight |
| F. Deionized Water | 2% by weight |

Add B to A and mix until homogeneous and clear. Add C to mixed A and B. Mix until homogenous and clear. Add D to mixed A, B and C, until homogeneous and clear. Add E at moderate agitation, until homogeneous and clear. Titrate with F if necessary to match refractive index of two phases.

A similar composition may be formed by substituting the polypropylene glycol component with a polyalkylene glycol such as polyethylene glycol (PEG) having an average molecular weight of about 400. Thus, a non-limiting example of such a formulation, made in a manner essentially similar to that of the formulation shown above, may comprise:

| | |
|---|---|
| A. Deionized Water | 30% by weight |
| B. polyethylene glycol (PEG 400) | 35% by weight |
| C. PVP/vinyl acetate copolymer | 10% by weight |
| D. Paste | 23% by weight |
| E. Propylene Glycol | 2% by weight |
| F. Deionized Water | 2% by weight |

Exemplary Compositions

Composition 1

| Component | Ingredient | % wt |
|---|---|---|
| A | Cosmetic Fluid ® 3506 (>about 50% cyclopentylsiloxane, about 35% (6 centistoke) dimethacone, about 15% dimethiconol) | 24.00 |
| | Seppic Gel ® 305 (polyacrylamide, $C_{13-14}$ isoparaffin and laureth-7 | 3.00 |
| B | Deionized Water | 30.00 |
| | Butylene Glycol | 40.00 |
| | Glydent Plus ® (DMDM hydrantoin, iodopropynyl butylcarbamate) | 0.15 |
| C | Deionized Water | 2.85 |
| D | Butylene Glycol | q.s. |

Assembly Steps

1) Mix component A until uniform.
2) Pre-mix component B adding one ingredient at a time until clear.
3) Add component B to component A very slowly until uniform.
4) Add component C to vessel in small increments at low agitation until batch appears clear.
5) Only if batch appears cloudy, add component D at very low agitation and in very small increments; titrate using butylenes glycol to match refractive index.

Composition 2

| Component | Ingredient | % wt |
|---|---|---|
| A | Chemsil ® K-51 (cyclopentylsiloxane, dimethacone/vinyl dimethicone crosspolymer) | 24.00 |
| | Simulgel ® 600 (acrylamide/sodium scryloyldimethyltaurate copolymer/isohexadecane/polysorbate 80) | 3.00 |
| B | Deionized Water | 30.00 |
| | Propylene Glycol | 40.00 |
| | Glydent Plus ® (DMDM hydrantoin, iodopropynyl butylcarbamate) | 0.15 |
| C | Deionized Water | 2.85 |
| D | Butylene Glycol | q.s. |

Assembly Steps

1) Mix component A until uniform.
2) Pre-mix component B adding one ingredient at a time until clear.
3) Add component B to component A very slowly until uniform.

4) Add component C to vessel in small increments at low agitation until batch appears clear.
5) Only if batch appears cloudy, add component D at very low agitation and in very small increments; titrate using butylenes glycol to match refractive index.

Composition 3

| Component | Ingredient | % wt |
| --- | --- | --- |
| A | Chemsil ® K-51 (cyclopentylsiloxane, dimethacone/vinyl dimethicone crosspolymer) | 24.00 |
|  | Simulgel ® SMS-88 (acrylamide/sodium scryloyldimethyltaurate copolymer/isohexadecane/polysorbate 80 | 3.00 |
| B | Deionized Water | 30.00 |
|  | Propylene Glycol | 40.00 |
|  | Glydent Plus ® (DMDM hydrantoin, iodopropynyl butylcarbamate) | 0.15 |
| C | Deionized Water | 2.85 |
| D | Butylene Glycol | q.s. |

Assembly Steps
1) Mix component A until uniform.
2) Pre-mix component B adding one ingredient at a time until clear.
3) Add component B to component A very slowly until uniform.
4) Add component C to vessel in small increments at low agitation until batch appears clear.
5) Only if batch appears cloudy, add component D at very low agitation and in very small increments; titrate using butylenes glycol to match refractive index.

Composition 4

| Component | Ingredient | % wt |
| --- | --- | --- |
| A | Chemsil ® K-51 (cyclopentylsiloxane, dimethacone/vinyl dimethicone crosspolymer) | 24.00 |
|  | Simulgel ® 600 (acrylamide/sodium acryloyldimethyltaurate copolymer/isohexadecane/polysorbate 80) | 3.00 |
| B | Deionized Water | 30.00 |
|  | Propylene Glycol | 40.00 |
|  | Glydent Plus ® (DMDM hydrantoin, iodopropynyl butylcarbamate) | 0.15 |
| C | Deionized Water | 2.85 |

Assembly Steps
1) Mix component A until uniform.
2) Pre-mix component B adding one ingredient at a time until clear.
3) Add component B to component A very slowly until uniform.
4) Add component C to vessel in small increments at low agitation until batch appears clear.
5) titrate using butylenes glycol to match refractive index only if needed.

Composition 5

| Component | Ingredient | % wt |
| --- | --- | --- |
| A | Chemsil ® K-51 (cyclopentylsiloxane, dimethacone/vinyl dimethacone crosspolymer) | 24.00 |
|  | Simulgel ® EG (sodium acrylate/sodium acryloyldimethyltaurate copolymer/isohexadecane/polysorbate 80) | 2.50 |
| B | Deionized Water | 30.00 |
|  | Propylene Glycol | 40.00 |
|  | Glydent Plus ® (DMDM hydrantoin, iodopropynyl butylcarbamate) | 0.15 |
| C | Deionized Water | 2.35 |

Assembly Steps
1) Mix component A until uniform.
2) Pre-mix component B adding one ingredient at a time until clear.
3) Add component B to component A very slowly until uniform.
4) Add component C to vessel in small increments at low agitation until batch appears clear.
5) titrate using butylene glycol to match refractive index only if needed.

Composition 6

| Component | Ingredient | % wt |
| --- | --- | --- |
| A | Chemsil ® K-51 (cyclopentylsiloxane, dimethacone/vinyl dimethicone crosspolymer) | 24.00 |
|  | Simulgel ® NS (hydroxyethyl acrylate/sodium scryloyldimethyl taurate copolymer/squalene/polysorbate 60) | 3.00 |
| B | Deionized Water | 30.00 |
|  | Propylene Glycol | 40.00 |
|  | Glydent Plus ® (DMDM hydrantoin, iodopropynyl butylcarbamate) | 0.15 |
| C | Deionized Water | 2.85 |

Assembly Steps
1) Mix component A until uniform.
2) Pre-mix component B adding one ingredient at a time until clear.
3) Add component B to component A very slowly until uniform.
4) Add component C to vessel in small increments at low agitation until batch appears clear.
5) titrate using butylenes glycol to match refractive index only if needed.

Composition 7

| Component | Ingredient | % wt |
| --- | --- | --- |
| A | Deionized Water | 30.00 |
| B | Propylene Glycol | 40.00 |
| C | Sepinov ® EMT-10 (acrylamide/sodium | 2.5 |

| Component | Ingredient | % wt |
|---|---|---|
| | acryloyldimethyltaurate copolymer/isohexadecane/polysorbate 80 | |
| D | Chemsil ® K-51 (cyclopentylsiloxane, dimethacone/vinyl dimethacone crosspolymer) | 24.00 |
| E | Glydent Plus ® (DMDM hydrantoin, iodopropynyl butylcarbamate) | 0.15 |
| F | Propylene Glycol | 2.85 |
| G | Deionized Water | 0.50 |

Assembly Steps
1) Add component B to component A and mix until uniform.
2) Disperse C to A and B and mix until uniform.
3) Add component D to mixed components A, B and C very slowly until uniform.
4) Add component E to vessel at low agitation.
5) Titrate using butylene glycol to match refractive index only if needed to obtain clarity.
6) Add deionized water if more clarity is needed.

| Component | Ingredient | % wt |
|---|---|---|
| A | Chemsil ® K-51 (cyclopentylsiloxane, dimethacone/vinyl dimethicone crosspolymer) | 25.00 |
| | Simulgel ® NS (hydroxyethyl acrylate/sodium scryloyldimethyl taurate copolymer/squalene/polysorbate 60) | 3.00 |
| B | Deionized Water | 30.00 |
| | Propylene Glycol | 40.00 |
| | Glydent Plus ® (DMDM hydrantoin, iodopropynyl butylcarbamate) | 0.15 |
| C | Deionized Water | 1.85 |

Composition 8
Assembly Steps
1) Mix component A until uniform.
2) Pre-mix component B adding one ingredient at a time until clear.
3) Add component B to component A very slowly until uniform.
4) Add component C to vessel in small increments at low agitation until batch appears clear.
5) titrate using butylene glycol to match refractive index only if needed.

Composition 9 (Prototype)

| Component | Ingredient | % wt |
|---|---|---|
| A | Deionized Water | 33.00 |
| B | Propylene Glycol | 40.00 |
| C | Sepinov ® EMT-10 (hydroxyethyl acrylate/sodium acryloyldimethyltaurate copolymer) | 1.0 |
| D | Chemsil ® K-51 (cyclopentylsiloxane, dimethacone/vinyl dimethacone crosspolymer) | 24.00 |
| E | Glydent Plus ® (DMDM hydrantoin, iodopropynyl butylcarbamate) | 0.15 |
| F | Propylene Glycol | 1.85 |

Assembly Steps
1) Add component B to component A and mix until uniform.
2) Disperse C to A and B and mix until uniform.
3) Add component D to mixed components A, B and C very slowly until uniform.
4) Add component E to vessel at low agitation.
5) Titrate using propylene glycol (or butylene glycol) to match refractive index only if needed to obtain clarity.

EXAMPLES

Example 1

Determination of Coefficient of Friction

Determination of friction was performed using the scratch stylus method. In this method, a series of scratches is made across a surface coated with the composition to be tested. The stylus, usually a diamond tip, is drawn across the sample's surface at a constant speed and a defined normal (perpendicular) force for a defined distance. The defined normal force may be constant or progressively increasing. The test may be performed using a low constant normal force and a ball rather than a diamond tip to minimize the wear or damage on the surface.

Compositions Tested Were:

TABLE 1

| Code | Trade Name | Components |
|---|---|---|
| G | KY INTRIGUE ® | All silicone personal lubricant made using dimethacone and dimethiconol |
| O | DM200 ® | A 200 centistoke dimethyl silicone fluid. |
| Q | CHEMSIL ® K-51 | cyclopentylsiloxane, dimethacone/vinyl dimethacone crosspolymer |
| P | Propylene Glycol | propylene glycol |
| E | Composition 9 (Prototype) | Washable personal lubricant containing propylene glycol, hydrophilic component containing (hydroxyethyl acrylate/sodium acryloyldimethyltaurate copolymer) and hydrophobic component containing (cyclopentylsiloxane, dimethacone/vinyl dimethacone crosspolymer) |

TABLE 1-continued

| Code | Trade Name | Components |
|---|---|---|
| M | ASTROGLIDE ® | Strictly water-based personal lubricant |
| L | KY JELLY ® | Strictly water-based personal lubricant |
| K | WET LIGHT ® | Strictly water-based personal lubricant |
| N | Water | Water |

Test parameters were as follows:
Load Type: Constant
Load: 100 mN
Scratch Length: 5 mm
Speed: 25 mm/min
Cantilever: ST-148
Static Partner Size: Diameter 6 mm
Static partner Material: SS440 grade 25

For all samples except E, L and Q: 2-3 drops of lubricant were placed in the center of a microscope glass slide and spread over an approximate area of 25 mm×15 mm using the wood part of a cotton swab. One location was measured (3 passes back and forth along a same path for a total of 6 passes over a single spot).

For samples E, L and Q: a thin layer of lubricant was deposited on a microscope slide by putting lubricant between two glass slides and applying pressure on the glass. Friction at one location was measured (3 passes back and forth along a same path for a total of 6 passes over a single spot).

Table 2 below shows the coefficient of friction, μ, measured between 0.50 mm and 4.50 mm.

TABLE 2

| | Scan #1 | Scan #2 | Scan #3 | Scan #4 | Scan #5 | Scan #6 | Average |
|---|---|---|---|---|---|---|---|
| Glass | 0.008 | 0.138 | 0.047 | 0.154 | 0.037 | 0.161 | 0.104 ± 0.055 |
| Sample E | 0.133 | 0.169 | 0.175 | 0.204 | 0.183 | 0.238 | 0.184 ± 0.035 |
| Sample G | 0.081 | 0.122 | 0.037 | 0.123 | 0.031 | 0.125 | 0.087 ± 0.044 |
| Sample K | 0.145 | 0.164 | 0.195 | 0.265 | 0.302 | 0.389 | 0.243 ± 0.093 |
| Sample L | 0.150 | 0.209 | 0.141 | 0.254 | 0.163 | 0.306 | 0.204 ± 0.066 |
| Sample M | 0.174 | 0.192 | 0.203 | 0.218 | 0.209 | 0.202 | 0.200 ± 0.015 |
| Sample N | 0.200 | .0406 | 0.415 | 0.614 | 0.523 | 0.661 | 0.470 ± 0.167 |
| Sample O | 0.107 | 0.097 | 0.095 | 0.092 | 0.100 | 0.088 | 0.097 ± 0.007 |
| Sample P | 0.208 | 0.155 | 0.145 | 0.159 | 0.125 | 0.171 | 0.161 ± 0.028 |
| Sample Q | 0.117 | 0.119 | 0.105 | 0.107 | 0.101 | 0.110 | 0.110 ± 0.007 |

As a result of these data it is possible to place the compositions in the order from lowest coefficient of friction to highest coefficient of friction, with Sample G (the lowest coefficient of friction)<Sample O<Sample Q<Sample P<Sample E<Sample M<Sample L<Sample K<Sample N (the highest coefficient of friction tested in this experiment)

A similar set of experiments was done using other lubricants, as indicated, and the results are shown below based upon a single stylus pass.

TABLE 3

| Nature of Lubricant | Trade Name | Coefficient of Friction |
|---|---|---|
| Silicone-based | KY Intrigue ® | 0.081 |
| Silicone-based | Pjur Woman ® | 0.091 |
| Silicone-based | I.D. ® | 0.1 |
| Water-based | KY Touch Massage ® | 0.127 |
| Water-based | Wet Warming ® | 0.133 |
| Water/silicone-based | Composition 9 (Prototype) | 0.143 |
| Water-based | XO-Therm ™ HV | 0.173 |
| Water-based | KY Warming ® | 0.174 |
| Water-based | Astroglide Warming ® | 0.208 |

These lubricants have ingredients as follows:
KY Intrigue
Dimethicone and dimethiconol
Pjur Woman
Cyclopentasiloxane, dimethicone and dimethiconol
I.D. Millennium
Cyclomethicone, dimethicone and dimethiconol
KY Touch Massage
Propylene glycol, polyethylene glycol, lactic acid and hydroxypropylcellulose
Wet Warming
Propylene glycol, glycerin, diglycerin, honey, acacia senegal gum, sclerotium gum, water, propylparaben, methylparaban and diazolidinyl urea
CRL-03-108C
(Composition 9 (Prototype)
XO-Therm HV
Polyalkylene glycol, PVP
KY Warming
Propylene glycol, glycerin, purified honey and methylparaban
Astroglide Warming
Propylene glycol, glycerin, purified water, methylparaban and polyquat-15

The data show that the clear, washable lubricant compositions of the present invention, Composition 9 (Prototype) has an intermediate degree of lubricity (coefficient of friction), falling generally between the silicone-based lubricants, and the water-based lubricants, which generally appeared to have a somewhat lesser lubricity in this series of experiments than silicone-based lubricants.

Example 2

The ability of various lubricant compositions to stain different fabrics was assessed. Fabrics tested were 100% cotton, 100% satin, and 100% polyester.

On each fabric 2 oz. of each of the following silicone-based lubricant compositions (I.D. Millenium [cyclomethicone, dimethicone, dimethiconol]; KY Intrigue™ [dimethacone, dimethaconol]; Pjur® Eros [cyclopentasiloxane, dimethicone, dimethiconol], and Composition 9 (Prototype)) were gently rubbed into a labeled location on the fabric and allowed to sit overnight. The fabric was then washed in warm water using a standard laundry detergent on a normal cycle setting. The fabric was then laid out to air dry.

Following the washing, the fabric samples were observed for staining by the personal lubricant compositions. Of the fabric samples tested, the most easily visible results were obtained with 100% cotton, followed by 100% polyester; satin was the most difficult fabric upon which to clearly see the stains. In all cases stains were seen where the I.D., KY and Pjur products were spotted. In no case was a spot seen in the location where the Composition 9 (Prototype) was spotted.

In all cases the stain formed by the I.D. Intrigue was larger than that formed by Pjur Eros, which was larger than the stain formed by the I.D. Millenium sample; the ratios of the diameters of the stains were, on each fabric, approximately 1 to 1.25 to 1.75. This may be due at least in part by the viscosity of the lubricant.

Thus, Composition 9 (Prototype), which comprises a formulation of the present invention, is non-staining and appears to be washed entirely from cotton, satin and polyester fabrics under the conditions used in this experiment.

Example 3

Following a hot shower a man applies a shaving fluid comprising Composition 9 to his face as a shaving aid. The shaving fluid permits a close, lubricated shave that can be cleaned up using water, and leaves the facer feeling smooth and supple.

Example 4

A woman has dry, chapped skin during a summer heat wave. The woman applies a small amount of a skin conditioner comprising Composition 9 to her skin. The skin conditioner leaves her skin feeling refreshed and smooth, the clarity of the skin conditioner renders it invisible when worn, and it does not stain her clothing.

Example 5

It will understood by those of ordinary skill in the art that the compositions of the present invention are defined by the claims and that the specific composition of lubricants falling within the claims does not preclude the inclusion within the claims of other lubricant compositions having different specific component compositions than those exemplified.

Thus, for example, Composition 9, disclosed above, uses propylene glycol as "Component B", which, when mixed with Component A (water) is part of the hydrophilic component of the final formulation. Propylene glycol is also used in Composition 9 to titrate the refractive indices of the final formulation, although the disclosure also indicates that other hydrophilic alkylene glycols, such as butylene glycol, which has similar properties as a humectant and a hydrophilic agent with low toxicity, may alternatively be used in either capacity.

For clarity's sake, the hydrophilic component of the present invention may include a polyalkylene glycol instead of, or in addition to, the hydrophilic alkylene glycol. Thus, in an alternative embodiment, the propylene glycol component may be removed, and, for example, a polyalkylene glycol component used in its place. For example, a polyethylene glycol (PEG) component may be used. Preferably the polyethylene glycol component has an average molecular weight of between about 100 to about 800 Daltons, more preferably about 200 to about 600 Daltons, even more preferably about 300 to about 500 Daltons, or about 400 Daltons. In customary nomenclature, the average molecular weight is listed after the acronym "PEG", as in "PEG 400" for an average molecular weight of about 400 Daltons. Examples of such compositions are shown below.

Formulation 100

| Component | Ingredient | % wt |
|---|---|---|
| A | Deionized Water | 33.00 |
| B | PEG 400 | 40.00 |
| C | Sepinov ® EMT-10 (hydroxyethyl acrylate/ | 1.0 |

-continued

| Component | Ingredient | % wt |
|---|---|---|
| | sodium acryloyldimethyltaurate copolymer) | |
| D | Chemsil ® K-51 (cyclopentylsiloxane, dimethacone/vinyl dimethacone crosspolymer) | 24.00 |
| E | Glydent Plus ® (DMDM hydrantoin, iodopropynyl butylcarbamate) | 0.15 |
| F | Propylene Glycol | 1.85 |

Assembly Steps
1) Add component B to component A and mix until uniform.
2) Disperse C to A and B and mix until uniform.
3) Add component D to mixed components A, B and C very slowly until uniform.
4) Add component E to vessel at low agitation.
5) Titrate using propylene glycol to match refractive index only if needed to obtain clarity.

Formulation 200

| Component | Ingredient | % wt |
|---|---|---|
| A | Deionized Water | 33.00 |
| B | PEG 400 | 40.00 |
| C | Emusil WSL: Cyclopentasiloxane (and) Dimethicone (and) Vinyl Dimethicone Crosspolymer (and) Hydroxyethyl Acrylate (and) sodium Acryloyl Dimethyl Taurate Copolymer (and) Cyclohexasiloxane | 25.00 |
| F | Butylene Glycol | About 2% |

1) Add component B to component A and mix until uniform.
2) Add component C to mixed components A and B very slowly until uniform.
3) Titrate using butylene glycol to match refractive index only if needed to obtain clarity.

It will be understood that each and every patent, published patent application and item of non-patent literature cited in this patent application is hereby individually and expressly incorporated by reference in its entirety as part of this patent specification.

While this invention has been described with respect to various specific examples and embodiments, it is to be understood that the invention is not limited thereto and that it can be variously practiced within the scope of the following claims.

What is claimed is:
1. A method of making a substantially clear or translucent multiphasic personal lubricant composition comprising: mixing an immiscible mixture comprising
  a) a flowable polymeric hydrophobic silicone component phase including: a hydrophobic component selected from the group consisting of a dimethicone, phenyltrimethicone, a dimethiconol, and a vinyl dimethicone, and b) a flowable polymeric hydrophilic component phase containing greater than about 30% water, with a hydrophilic solution to a desired viscosity and adjusting the refractive index of the aqueous phase to substantially match that of the polymeric hydrophobic silicone component phase, if required, by the addition of a flowable hydrophilic agent, to yield a substantially clear or translucent multiphasic personal lubricant composition washable from fabric under normal laundry conditions.

2. The method of claim 1 wherein the refractive index is lowered by the addition of water as the flowable hydrophilic agent.

3. The method of claim 1 wherein the refractive index is raised by the addition of a glycol as the flowable hydrophilic agent.

4. A personal lubricant composition having two substantially immiscible phases in contact with each other comprising:
   a) a flowable polymeric hydrophilic component phase comprising a sodium acryloyl dimethyl taurate copolymer component and greater than about 30% water, and
   b) a flowable polymeric silicone component phase comprising a vinyl dimethicone crosspolymer component,
wherein the personal lubricant composition is substantially clear or translucent, is suitable for use as a sexual lubricant, and is washable from fabric under normal laundry conditions.

5. The composition of claim 4 wherein the polymeric hydrophilic component comprises an acrylate polymer component.

6. The composition of claim 5 wherein the acrylate polymer comprises a hydroxyethyl acrylate component.

7. The composition of claim 4 wherein the polymeric silicone component comprises a D5 cyclic or small linear dimethicone component.

8. The composition of claim 5 wherein the polymeric silicone component comprises a D5 cyclic or small linear dimethicone component.

9. The composition of claim 6 wherein the polymeric silicone component comprises a D5 cyclic or small linear dimethicone component.

10. The composition of claim 7 wherein the D5 cyclic or small linear dimethicone component comprises a cyclopentasiloxane component.

11. The composition of claim 9 wherein the D5 cyclic or small linear dimethicone component comprises a cyclopentasiloxane component.

12. A personal lubricant composition consisting essentially of two substantially immiscible phases in contact with each other comprising:
    a) a flowable polymeric hydrophilic component phase comprising greater than about 30% water, and
    b) a flowable polymeric silicone component phase,
wherein the personal lubricant composition is substantially clear or translucent, is suitable for use as a sexual lubricant, and is washable from fabric under normal laundry conditions.

13. The composition of claim 12 wherein the polymeric hydrophilic component comprises an acrylate polymer component.

14. The composition of claim 13 wherein the acrylate polymer comprises a hydroxyethyl acrylate component.

15. The composition of claim 12 wherein the polymeric silicone component comprises a D5 cyclic or small linear dimethicone component.

16. The composition of claim 13 wherein the polymeric silicone component comprises a D5 cyclic or small linear dimethicone component.

17. The composition of claim 14 wherein the polymeric silicone component comprises a D5 cyclic or small linear dimethicone component.

18. The composition of claim 13 wherein the D5 cyclic or small linear dimethicone component comprises a cyclopentasiloxane component.

19. The composition of claim 17 wherein the D5 cyclic or small linear dimethicone component comprises a cyclopentasiloxane component.

20. The method of claim 1 wherein the respective refractive indices of the polymeric hydrophilic component phase and the polymeric silicone component phase and adjusted to differ by no more than about 0.001 units.

21. The method of claim 1 wherein said mixing step further comprises adding a component comprising at least one member of the group consisting of a scent and a flavor.

22. A personal lubricant composition comprising two substantially immiscible phases in contact with each other comprising:
    a) a polymeric hydrophilic component phase comprising a sodium acryloyl dimethyl taurate copolymer component and a hydroxyethyl acrylate component, and
    b) a polymeric silicone component phase comprising a vinyl dimethicone crosspolymer component and a cyclopentylsiloxane component,
wherein the personal lubricant composition is substantially clear or translucent, is suitable for use as a sexual lubricant, and is washable from fabric under normal laundry conditions.

* * * * *